United States Patent [19]

Eller et al.

[11] 4,152,118

[45] May 1, 1979

[54] COPPER MERCAPTIDES AS SULFUR DIOXIDE INDICATORS

[75] Inventors: Phillip G. Eller; Gregory J. Kubas, both of Los Alamos, N. Mex.

[73] Assignee: The United States of America as represented by the United States Department of Energy, Washington, D.C.

[21] Appl. No.: 916,181

[22] Filed: Jun. 16, 1978

[51] Int. Cl.$^2$ .................. G01N 31/22; G01N 21/12
[52] U.S. Cl. .......................... 23/232 R; 260/438.1; 422/56; 422/86
[58] Field of Search ............... 260/438.1; 23/232 R; 422/56, 86

[56] References Cited

U.S. PATENT DOCUMENTS

| | | | |
|---|---|---|---|
| 3,626,742 | 12/1971 | Hogan et al. | 23/232 D |
| 3,997,296 | 12/1976 | Miller | 23/232 R |

OTHER PUBLICATIONS

Placa et al., *Inorganic Chemistry*, vol. 5, No. 3, Mar. 1966, pp. 405–410.
Snow et al., *Inorganic Chemistry*, vol. 12, No. 1, 1973, pp. 224–229.
Eller et al., *Inorganic Chemistry*, vol.15, No. 10, 1976, pp. 244–2445.
Eller et al., *Inorganic Chemistry*, vol. 16, No. 10, 1977, pp. 2454–2462.

*Primary Examiner*—Arnold Turk
*Attorney, Agent, or Firm*—Dean E. Carlson; Edward C. Walterscheid

[57] ABSTRACT

Organophosphine copper(I) mercaptide complexes are useful as convenient and semiquantitative visual sulfur dioxide gas indicators. The air-stable complexes form 1:1 adducts in the presence of low concentrations of sulfur dioxide gas, with an associated color change from nearly colorless to yellow-orange. The mercaptides are made by mixing stoichiometric amounts of the appropriate copper(I) mercaptide and phosphine in an inert organic solvent.

7 Claims, No Drawings

COPPER MERCAPTIDES AS SULFUR DIOXIDE INDICATORS

BACKGROUND OF THE INVENTION

The invention described herein relates to organophosphine, arsine, or stibine copper(I) mercaptide complexes of the general formula $Cu(MR_3)_n(SR')$ where $M = P$, As, or Sb and R and R' are organo groups and their use as $SO_2$ indicators and scavengers.

Sulfur dioxide is a major pollutant in a great variety of industrial processes, and the monitoring of this gas is necessary for environmental, health, and engineering considerations. At this time, there are instrumental methods of direct $SO_2$ gas analysis but virtually no generally recognized dry chemical indicators.

SUMMARY OF THE INVENTION

We have found that organophosphine copper(I) mercaptide complexes readily undergo adduct formation with $SO_2$ in low concentration, with an associated color change from essentially colorless to yellow or bright orange. The arsines and stibines react similarly. Accordingly, in its broad scope, our invention encompasses a method of detecting $SO_2$ in an ambient atmosphere which comprises (a) contacting the atmosphere with a complex of the general formula $Cu(MR_3)_n(SR')$ where M is P, As, or Sb, n is 1 to 3, and R and R' represent an unsubstituted alkyl, cycloalkyl, aralkyl, or aryl group or such a group containing inert substituents, and (b) monitoring any color change produced in the complex as the result of formation of an $SO_2$ adduct. The mercaptides are made by mixing stoichiometric amounts of the appropriate copper(I) mercaptide and a phosphine, arsine, or stibine in an inert organic solvent. The resultant complexes serve as indicators for $SO_2$ concentrations at least as low as 100 ppm when in the solid state, solution, or suspended on a filter paper support. The $SO_2$ is bound reversibly, and the adducts possess low dissociation pressures ($\sim 1$ torr) at ambient temperature and high dissociation pressures at 100° C. Thus, the copper mercaptides disclosed herein can also be used as scavengers for $SO_2$ in process gases by merely heating them to release the bound $SO_2$.

DESCRIPTION OF THE PREFERRED EMBODIMENTS

The Lewis acid character of $SO_2$ toward a wide variety of main group bases is well known. However, only a few compounds have been reported in which $SO_2$ bonds to coordinated ligands. We have now found that organophosphine copper(I) complexes of the general formula $Cu(PR_3)_n(SR')$ readily react with $SO_2$ at room temperature to form bright orange to yellow adducts. Since the $Cu(PR_3)_n(SR')$ complexes are nearly colorless, the formation of the brightly colored adducts provides a ready indication of the presence of $SO_2$.

As a consequence, these complexes are easily adaptable to a visual detection method for low concentrations of $SO_2$ which is specific, inexpensive, semiquantitative, rapid, and simple. Furthermore, they can be regenerated after use merely by allowing them to stand in $SO_2$-free air or by mild heating at $\sim 100°$ C., whereupon the bound $SO_2$ is released. However, removal of $SO_2$ from the adducts can best be effected by dissolving them in organic solvents and slowly removing solvent in vacuo. In a preferred embodiment, a concentrated solution of the complex is evaporated on a strip of filter paper which then serves as the detector. Exposure of the filter paper to air containing $SO_2$ produces a color change almost immediately, with the variation in color being dependent on the amount of $SO_2$ and the length of exposure.

Alternatively, the complexes may be used as wet rather than dry $SO_2$ detectors in that the air or other gas containing $SO_2$ may be bubbled through a solution of the complex. The solution then takes on the characteristic orange or yellow color as the adduct is formed.

As used in this specification, in the general formula $Cu(PR_3)_n(SR')$ n is 1–3, and R and R' represent an unsubstituted alkyl, cycloalkyl, aralkyl, or aryl group or such a group containing inert substituents. For the types of groups which may generally be represented by R and R', see U.S. Pat. No. 3,336,392 and the discussion therein with respect to formula III of that patent which is incorporated herein by reference. Specifically, R and R' include but are not limited to Me, Et, Ph, Bz, Cy, and $C_6F_5$ where Me is methyl, Et is ethyl, Ph is phenyl, Bz is benzyl, and Cy is cyclohexyl. It should be noted that while the phosphine complexes are preferred, $SO_2$ adducts also readily form with the arsine and stibine complexes.

The nature of the organic substituents on both the phosphine and mercaptide ligands influences the stability of the $SO_2$ complexes. It appears that adducts with ligands of high basicity are more stable than those with less basic ligands, which is not surprising since the $SO_2$ is behaving as a Lewis acid toward the $XR^-$ group.

The $Cu(PR_3)_n(SR')$ complexes are easily prepared by dissolving the known polymeric mercaptides, $CuSR'$, in chloroform or another appropriate organic solvent containing n (in some cases n+1) moles of phosphine ($PR_3$) per mole of $CuSR'$. The $CuSR'$ is readily prepared by the method of Ducan, Ott, and Reid, Ind. & Eng. Chem. 23, 3181 (1931). In some instances it is difficult to crystallize the $Cu(PR_3)_n(SR')$ species from solution due to oil formation. However, addition of excess $SO_2$ gas to the solution will induce crystallization of yellow to orange $SO_2$ adducts, $Cu(PR_3)_n(SR')(SO_2)$, which, e.g., on controlled heating in vacuo, will release $SO_2$ and yield solid $Cu(PR_3)_n(SR')$. To the extent that certain of the phosphines may be oxygen sensitive, the complexes of these phosphines are readily prepared in an inert atmosphere. If the complexes are soluble in the organic solvent used, addition of a straight chain alkane such as n-heptane or n-hexane facilitates their removal from the reaction mixture.

EXAMPLE I

A mixture of $PBz_3$ and $Cu(SPh)$ in a 3:1 molar ratio was stirred in $CHCl_3$ (minimum quantity to dissolve $PBz_3$) under nitrogen until the mercaptide dissolved (10–30 minutes). The resulting solution was treated with a small amount of decolorizing carbon and filtered. Excess n-heptane (n-hexane can also be used) was added until precipitation of the nearly white $Cu(PBz_3)_2(SPh)$ was complete. The flocculent solid was collected by filtration, washed with hexane, and dried in vacuo at 50° C. Elemental analysis (Theory for $C_{48}H_{47}P_2SCu$: %C, 73.8; %H, 6.1. Found: %C, 72.4; %H, 5.9) indicated the composition of the solid to be as stated. Yield was essentially quantitative.

EXAMPLE II

When prepared in accordance with Example I, certain of the $Cu(PR_3)_n(SR')$ complexes are obtained as oils. To convert such oils to solids, the complex is dissolved in diethyl ether and $SO_2$ is slowly bubbled through the solution. A bright orange color develops immediately and crystals of the 1:1 $SO_2$ adduct begin to deposit. The product is collected on a filter, washed with $SO_2$-saturated ether, and dried in a stream of $SO_2$. The yields of $Cu(PR_3)_n(SR')(SO_2)$ depend on solubility and other factors but are generally 60–90%. Complexes which are readily obtained in this way include those for $n=3$, $R_3=MePh_2$ ($R'=Ph$) and $n=2$, $R_3=Ph_3$ ($R'=Me$, Et, $C_6F_5$), $R_3=MePh_2$ ($R'=Me$), $R_3=Bz_3$ ($R'=Et$, Ph), and $R_3=Cy_3$ ($R'=Me$, Ph, Cy). The $SO_2$ bonds to the mercaptide sulfur in these adducts, as demonstrated by the x-ray crystal structure of $Cu(PPh_2Me)_3(SPh)(SO_2)$. See Eller and Kubas, J. Amer. Chem. Soc. 99, 4346 (June 22, 1977), which is incorporated herein by reference.

Generally solid $SO_2$-free complexes can be readily obtained by heating the adducts in vacuo to 100°–150° C. Slight loss of phosphine may occur, especially at higher temperatures. This, however, does not appear to affect the ability of the complex to form $SO_2$ adducts. The $SO_2$ is also released slowly by dissolving the adducts in organic solvents and removing solvent in vacuo at ambient temperature.

EXAMPLE III

The solid mercaptides and their solutions in organic solvents immediately turn yellow to orange when exposed to gaseous $SO_2$, even in low concentrations. A concentrated solution of $Cu(PCy_3)_2(SPh)$ in $CHCl_3$ was evaporated on a strip of filter paper. Exposure of the paper to air-$SO_2$ mixtures containing as little as 100 ppm $SO_2$ produced a substantial yellow coloration in the paper after about 3 minutes. A detectable color change occurred almost immediately and was more intense upon exposure of the paper to higher concentrations (>1000 ppm), thus indicating that semi-quantitative measurements are possible. Removal of the test strips from the $SO_2$-containing environment to the normal laboratory atmosphere resulted in a slow fading of color. After 2–3 days, the strips were once again nearly colorless and reusable since a new exposure to $SO_2$ gave substantially the same color change as before. High concentrations of nitrogen oxides (NO and/or $NO_2$) darkened the test strips, but did not give a yellow or orange coloration. $Cu(PPh_2Me)_3(SPh)$-impregnated filter paper gave similar results. Although there appears to be some variation in the lower limit of sensitivity of the various complexes, this variation may be used for quantitative measurements in that a test paper can be impregnated with calibrated bands of complexes with different continuous ranges of sensitivity.

The foregoing examples are not intended in any way to limit the scope of the invention but rather are presented for the purpose of meeting the enablement and best most requirements of 35 U.S.C. 112. The scope of the invention is as set forth in the Summary of the Invention and the broad claims appended hereto.

What we claim is:

1. A method of detecting $SO_2$ in an ambient atmosphere which comprises (a) contacting said atmosphere with a complex of the general formula $Cu(MR_3)_n(SR')$ wherein M is P, As, or Sb, n is 1 to 3, and R and R' represent an unsubstituted alkyl, cycloalkyl, aralkyl, or aryl group, and (b) monitoring any color change produced in the complex as the result of the formation of an $SO_2$ adduct.

2. The method of claim 1 wherein M is P.

3. The method of claim 2 wherein said complex is in solution and said atmosphere is passed through said solution.

4. The method of claim 2 wherein said complex is a solid disposed on a suitable substrate.

5. The method of claim 4 wherein a plurality of said complexes having different sensitivities are disposed in a desired sequence on said substrate.

6. The method of claim 3 or 4 wherein R and R' are methyl, ethyl, phenyl, cyclohexyl, or $C_6F_5$.

7. A detector for $SO_2$ in an ambient atmosphere which comprises $Cu(PR_3)_n(SR')$ disposed on a suitable substrate, wherein n is 1 to 3, and R and R' represent an unsubstituted alkyl, cycloalkyl, aralkyl, or aryl group.

* * * * *